United States Patent
Russell

(10) Patent No.: US 9,267,883 B2
(45) Date of Patent: Feb. 23, 2016

(54) SYSTEM AND METHOD OF MONITORING COMPOSITION OF A FLOW OF BREATHABLE GAS USING A DETECTOR AND EMITTER POSITIONED ON THE SAME SIDE OF THE FLOW OF BREATHABLE GAS

(71) Applicant: KONINKLIJKE PHILIPS N.V., Eindhoven (NL)

(72) Inventor: James Russell, Bellevue, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/362,725

(22) PCT Filed: Nov. 29, 2012

(86) PCT No.: PCT/IB2012/056831
§ 371 (c)(1),
(2) Date: Jun. 4, 2014

(87) PCT Pub. No.: WO2013/088289
PCT Pub. Date: Jun. 20, 2013

(65) Prior Publication Data
US 2014/0361176 A1 Dec. 11, 2014

Related U.S. Application Data

(60) Provisional application No. 61/576,594, filed on Dec. 16, 2011.

(51) Int. Cl.
| | | |
|---|---|---|
| G01J 5/02 | (2006.01) |
| G01N 21/3504 | (2014.01) |
| G01N 21/03 | (2006.01) |
| G01N 21/85 | (2006.01) |
| A61B 5/083 | (2006.01) |
| A61M 16/10 | (2006.01) |
| G01N 33/00 | (2006.01) |
| G01N 33/50 | (2006.01) |

(52) U.S. Cl.
CPC .......... *G01N 21/3504* (2013.01); *A61B 5/0836* (2013.01); *A61M 16/1005* (2014.02); *G01N 21/031* (2013.01); *G01N 21/85* (2013.01); *G01N 33/0027* (2013.01); *G01N 33/50* (2013.01); *A61M 2016/102* (2013.01); *G01N 2021/8578* (2013.01); *G01N 2201/0636* (2013.01)

(58) Field of Classification Search
CPC .................................................. G01N 21/3504
See application file for complete search history.

(56) References Cited

U.S. PATENT DOCUMENTS

| | | |
|---|---|---|
| 6,190,327 B1 | 2/2001 | Isaacson et al. |
| 2002/0029003 A1 | 3/2002 | Mace et al. |
| 2006/0009707 A1* | 1/2006 | Daniels et al. ............... 600/532 |

FOREIGN PATENT DOCUMENTS

| | | |
|---|---|---|
| GB | 2164743 A | 3/1986 |
| WO | 2007103855 A2 | 9/2007 |

* cited by examiner

*Primary Examiner* — David Porta
*Assistant Examiner* — Hugh H Maupin

(57) ABSTRACT

A gas measurement module (16) for use with an airway adapter (22) is configured such that both an emitter (48) and a detector (52, 54) are disposed on the same side of a sampling chamber (46) formed within the airway adapter. Optical elements (56) that guide electromagnetic radiation from the emitter back and forth across the sampling chamber to the detector include at least one toric element. The at least one toric element compensates for a tilted folding mirror positioned on a side of the sampling chamber opposite from the emitter and the detector.

15 Claims, 7 Drawing Sheets

SYSTEM AND METHOD OF MONITORING COMPOSITION OF A FLOW OF BREATHABLE GAS USING A DETECTOR AND EMITTER POSITIONED ON THE SAME SIDE OF THE FLOW OF BREATHABLE GAS

CROSS-REFERENCE TO PRIOR APPLICATIONS

This application is the U.S. National Phase application under 35 U.S.C. §371 of International Application No. PCT/IB2012/056831, filed on Nov. 29, 2012, which claims the benefit of U.S. Provisional Patent Application No. 61/576,594, filed on Dec. 16, 2011. These applications are hereby incorporated by reference herein.

BACKGROUND

1. Field

The present disclosure pertains to a method and apparatus for monitoring composition of a flow of breathable gas using an emitter and detector that are located on the same side of the flow of breathable gas.

2. Description of the Related Art

There are existing systems configured to monitor composition of flows of breathable gas being delivered to subjects. Some such systems rely on optical detection of composition. Typically, a beam of electromagnetic radiation is transmitted through a sample of the flow of breathable gas in question, and an optical detector on the other side measures a one or more parameters of the electromagnetic radiation after it has passed through the flow of breathable gas. The one or more parameters may include, for example, an optical band edge, band transmission, or band absorption. Such arrangements are known as non-dispersive (ND) systems.

SUMMARY

Accordingly, one or more aspects of the present disclosure relate to a gas measurement module configured to monitor composition of a flow of breathable gas within a respiratory circuit that is in fluid communication with an airway of a subject. In some embodiments, the gas measurement module comprises an emitter, a detector, and optical elements. The emitter is configured to emit infrared electromagnetic radiation. The detector is configured to generate output signals conveying information related to one or more parameters of electromagnetic radiation that becomes incident thereon. The optical elements are configured to guide the electromagnetic radiation emitted by the emitter into a sampling chamber through a first side. The sampling chamber has a first opening and a second opening, and is configured to form a flow path between the first opening and the second opening such that the flow of breathable gas within the respiratory circuit passes therethrough. The optical elements are configured to guide the emitted electromagnetic radiation through the first side of the sampling chamber, across the sampling chamber to a second side of the sampling chamber that is opposite to the first side of the sampling chamber, back across the sampling chamber to the first side of the sampling chamber, and onto the detector such that the output signals generated by the detector convey information related to one or more parameters of the emitted electromagnetic radiation that has traversed the sampling chamber and the flow of breathable gas therein twice. At least one of the optical elements is a toric element.

Yet another aspect of the present disclosure relates to a method of monitoring composition of a flow of breathable gas within a respiratory circuit that is in fluid communication with an airway of a subject. In some embodiments, the method comprises emitting infrared electromagnetic radiation; guiding the electromagnetic radiation emitted by the emitter into a sampling chamber through a first side, across the sampling chamber to a second side of the sampling chamber that is opposite to the first side of the sampling chamber, back across the sampling chamber to the first side of the sampling chamber, and onto the detector, wherein the sampling chamber has a first opening and a second opening, and is configured to form a flow path between the first opening and the second opening such that the flow of breathable gas within the respiratory circuit passes therethrough such that the electromagnetic radiation passes back and forth across the flow path and the flow of breathable gas therein, and wherein the guiding is performed in part by at least one toric optical element; and generating output signals conveying information related to one or more parameters of the electromagnetic radiation that has traversed the sampling chamber and the flow of breathable gas therein twice.

Still another aspect of present disclosure relates to a system for monitoring composition of a flow of breathable gas within a respiratory circuit that is in fluid communication with an airway of a subject. In some embodiments, the system comprises means for emitting infrared electromagnetic radiation; means for generating output signals conveying information related to one or more parameters of electromagnetic radiation that becomes incident thereon; and means for guiding the electromagnetic radiation emitted by the emitter into a sampling chamber through a first side, across the sampling chamber to a second side of the sampling chamber that is opposite to the first side of the sampling chamber, back across the sampling chamber to the first side of the sampling chamber, and onto the means for generating such that the output signals convey information related to one or more parameters of electromagnetic radiation that has traversed the sampling chamber and the flow of breathable gas twice, wherein the sampling chamber has a first opening and a second opening, and is configured to form a flow path between the first opening and the second opening such that the flow of breathable gas within the respiratory circuit passes therethrough such that the electromagnetic radiation passes back and forth across the flow path and the flow of breathable gas therein, and wherein the means for guiding includes at least one toric optical element.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
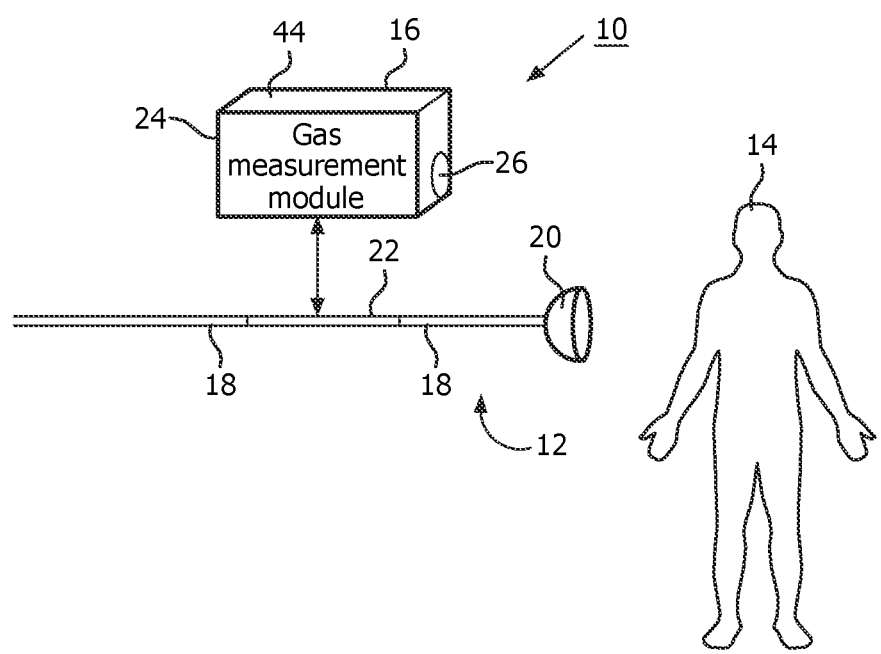
FIG. 1 is a system configured to monitor composition of a flow of breathable gas being delivered to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to analyze the composition of gas within a respiratory circuit 12 from which a subject 14 may receive ventilation therapy. In one embodiment, the respiratory circuit 12 is connected at one end to a pressure generator configured to generate a pressurized flow of breathable gas for delivery to the airway of subject 14 through respiratory circuit 12. However, this is not intended to be limiting. In one embodiment, system 10 includes a gas measurement module 16.

The respiratory circuit 12 includes a circuit conduit 18 and a subject interface appliance 20. In a number of different therapeutic scenarios, an airway of subject 14 is engaged to place respiratory circuit 12 in fluid communication with the airway of subject 14. The airway of subject 14 is engaged, and placed in fluid communication with respiratory circuit 12, by subject interface appliance 20. The subject interface appliance 20 may engage one or more orifices of the airway of subject 14 in a sealed or unsealed manner. Some examples of subject interface appliance 20 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

The circuit conduit 18 is configured to convey gas toward and away from subject interface appliance 20. By way of non-limiting example, circuit conduit 18 may include a flexible conduit. For the purposes of this disclosure, circuit conduit 18 is not necessarily limited to a tubular member that conveys pressurized gas flows to and/or from subject interface appliance 20. The circuit conduit 18 may include any hollow body, container, and/or chamber placed in fluid communication with the airway of subject 14 by subject interface appliance 20.

Figure 2:
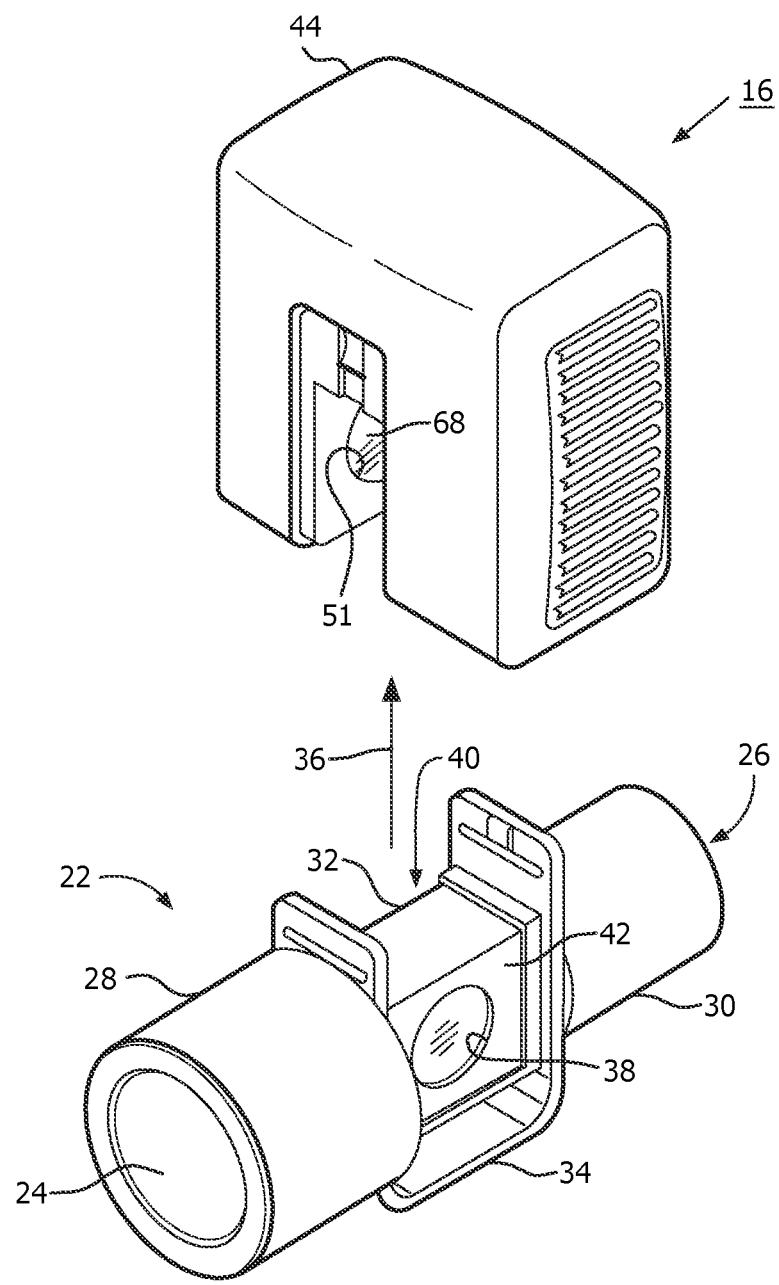
FIG. 2 is an airway adapter and gas measurement module.

The circuit conduit 18 includes a dock to which gas measurement module 16 can be removably coupled. The dock is formed in some embodiments by an airway adapter 22 included in circuit conduit 18. By way of illustration, FIG. 2 is an exploded view of airway adapter 22 and gas measurement module 16. Airway adaptor 22 includes a first opening 24 and a second opening 26, and is configured to form a flow path therebetween such that the flow of breathable gas within respiratory circuit 12 is conveyed through airway adapter 22. Airway adapter 22 can be a one-piece unit molded from Valox polyester and/or other polymers. Airway adapter 22 has a generally parallelepipedal center section 32 and two cylindrical end sections 28 and 30 that form first opening 24 and second opening 26, respectively. End sections 36 and 38 are axially aligned with center section 32.

The central section 32 of airway adapter 22 provides a seat for gas measurement module 16. An integral, U-shaped casing element 34 positively locates gas measurement module 16 endwise of airway adapter 22 and, also, in that transverse direction indicated by arrow 36 in FIG. 1. Arrow 36 also shows the direction in which airway adapter 22 is displaced to assemble it to gas measurement module 16. Windows 38 are formed in the center section 32 of airway adapter 22 on a first side 40 and a second side 42 of airway adapter 22. Windows 38 are formed from one or more materials that are optically transmissive for infrared electromagnetic radiation. With gas measurement module 16 assembled to airway adapter 22, these windows 38 are aligned along an optical path that is discussed further herein. That optical path extends from first side 40 to second side 42 transversely across the flow path formed by airway adapter 22 and the gas(es) flowing therethrough.

The gas measurement module 16 is configured to analyze the composition of gas within respiratory circuit 12. The gas measurement module 16 includes a housing 44 that houses and/or carries optical and/or electronic components that facilitate analysis of the composition of the gas within the sampling chamber formed by gas measurement module 16. Specifically, gas measurement module 16 is configured to direct infrared electromagnetic radiation across the sampling chamber of airway adapter 22 through windows 38, to receive the infrared electromagnetic radiation, and to generate output signals conveying information related to one or more parameters of the received electromagnetic radiation. The one or more parameters may include one or more of intensity, phase, flux, wavelength, and/or other parameters. These output signals can be used to determine composition of the gas within the sampling chamber.

Figure 3:
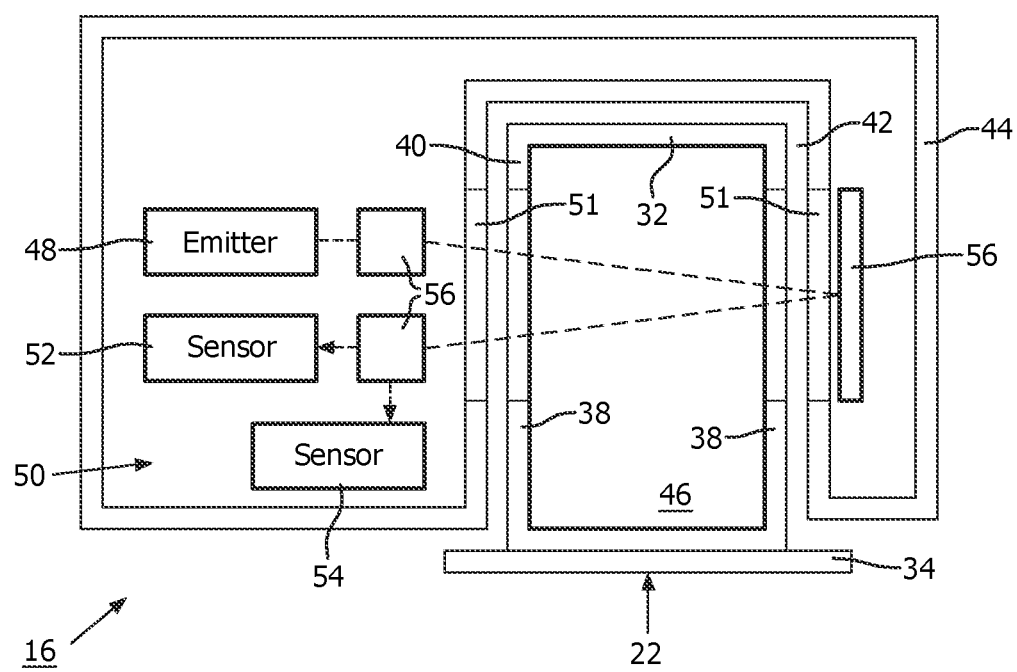
FIG. 3 is a is an airway adapter and gas measurement module.

By way of further illustration, FIG. 3 shows a schematic, sectional view of gas measurement module 16 and airway adapter 22 connected for operation. This view shows the sampling chamber 46 formed within airway adapter 22. As can be seen in each of FIGS. 2 and 3, housing 44 has a "U" shaped cross-section, and encloses a emitter 48, a detector 50, and/or other components. Two opposing legs of the "U" shaped housing 44 define opposite sides of a gap therebetween. In the leg on one side of the gap emitter 48 and detector 50 are disposed. The gas measurement module 16 also includes self-contained electronics disposed within the housing 44 (not shown).

Formed in housing 44 are a pair of windows 51 that align with windows 38 when gas measurement module 16 is docked with airway adapter 22 in the manner shown in FIG. 3. Windows 51 are formed from one or more materials that are transmissive for infrared electromagnetic radiation such that infrared electromagnetic radiation can pass along an optical path through both windows 38 and 51 to travel between sampling chamber 46 and the interior of housing 44.

Emitter 48 is a radiation source that produces broadband radiation including an "MWIR" (Mid-Wavelength InfraRed) band Infrared radiation generally refers to radiation occupying a band of wavelengths in the optical spectrum between 0.7 μm and 300 μm. "MWIR" generally refers to a mid-wavelength subset of the infrared radiation band between 3 μm and 8 μm. MWIR radiation emitted by emitter 48 includes a reference wavelength and a carbon dioxide wavelength ($\lambda_{REF}$ and $\lambda_{CO2}$, respectively). Emitter 48 may operate substantially as a blackbody for at least a portion of the spectrum (e.g., between 0.7 μm and 300 μm).

Detector 50 includes two separate photosensitive sensors 52 and 54. The basic principle of operation behind Capnometry/Capnography via detector 50 is that infrared radiation in a band around 4.275 μm experiences increasing absorption (when traveling a fixed-length path through a sample gas) with increasing carbon dioxide concentration—according to a reliably repeatable relationship. By way of comparison, the absorption of 3.681 μm infrared radiation under the same conditions is essentially unaffected by carbon dioxide concentration.

When the MWIR radiation from emitter 48 passes through the flow of breathable gas in sampling chamber 46, infrared radiation at $\lambda_{CO2}$ is attenuated according to the concentration of carbon dioxide in the flow of breathable gas. Infrared radiation at $\lambda_{REF}$, however, is unaffected by any carbon dioxide in the body of gas, and varies only with the intensity of the infrared radiation from emitter 48. Infrared radiation at $\lambda_{REF}$ is directed to sensor 52, while infrared radiation at $\lambda_{CO2}$ is directed to sensor 54. Since $\lambda_{REF}$ and $\lambda_{CO2}$ are fairly close together on the black-body radiation curve, the output signals of sensors 52 and 54, which are sensitive to IR electromagnetic radiation, will be approximately proportional to one another over small variations in source radiation intensity as long as carbon dioxide concentration in the body of gas remains constant. By "zeroing" detector 50 with $N_2$ (or with room air—after making appropriate compensation for residual carbon dioxide in the atmosphere), a reference ratio between the output signal levels from sensor 52 and sensor 54 is established. Whenever the ratio between the two signals is equal to this reference ratio, there is no carbon dioxide in sampling chamber 46. Any decrease in the output signal of sensor 54 relative to output signal of sensor 52 indicates a corresponding increase in the concentration of carbon dioxide in sampling chamber 46.

As can be seen in FIG. 3, gas measurement module 16 further includes optical elements 56 configured to guide electromagnetic radiation emitted by emitter 48 into sampling chamber 46 through first side 40 of sampling chamber 46. The electromagnetic radiation passes through sampling chamber 46 to second side 42, and is directed by optical elements 56 back toward first side 40. By guiding the electromagnetic radiation back through sampling chamber 46 back toward first side 40, the length of the optical path for the electromagnetic radiation through sampling chamber 46 is effectively doubled. This will tend to enhance absorption at $\lambda_{CO2}$ for a given level of carbon dioxide. This may provide various advantages over systems in which emitter 48 and detector 50 are positioned on opposite sides of sampling chamber 46. For example, the width of sampling chamber 46 may be reduced (e.g., to enhance form factor of airway adapter 22 and/or gas measurement module 16), the accuracy of gas measurement module 16 may be enhanced, and/or other advantages may be realized. As the electromagnetic radiation returns to first side 40, optical elements 56 receive the electromagnetic radiation back within housing 44 and direct the electromagnetic radiation onto sensors 52 and 54 for detection.

The configuration of gas measurement module 16 shown in FIG. 3, with both emitter 48 and sensors 52 and 54 in the same leg of the "U-shaped" housing 44 may have advantages over configurations in which emitter 48 is disposed in one leg of housing 44 while sensors 52 and 54 are disposed in the other leg. Such advantages include, for example, enhanced form factor (e.g., the leg without either emitter 48 or sensors 52 and 54 can be smaller and/or removed altogether), enhanced power or temperature management due to the proximity of emitter 48 with sensors 52 and 54, and/or other enhancements.

Figure 4:
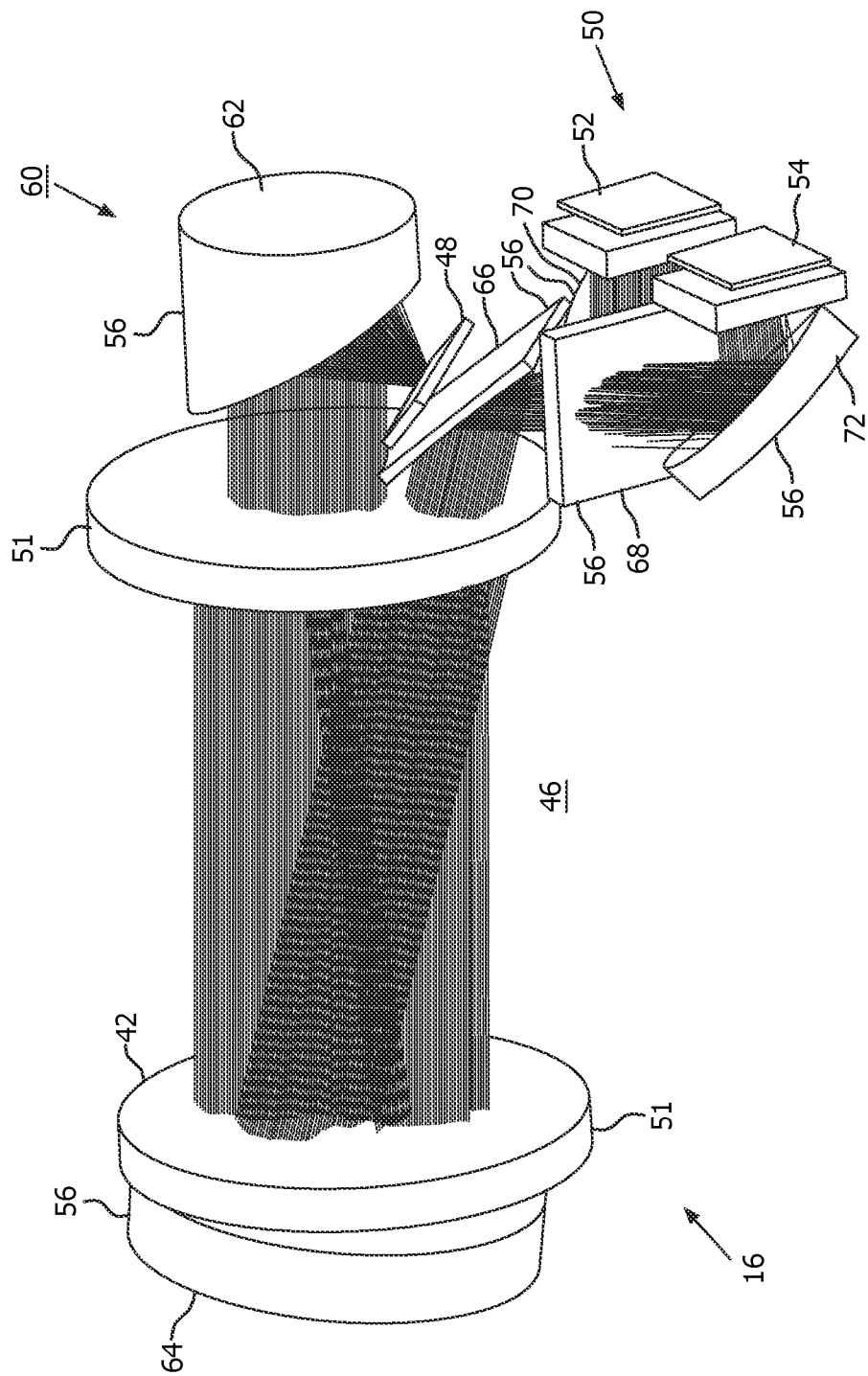
FIG. 4 illustrates an optical system of a gas measurement module.

FIG. 4 illustrates an optical system 60 of gas measurement module 16. Although an airway adapter is not shown in FIG. 4, windows 51 would be aligned with corresponding windows 38 of airway adapter 22 (shown in FIGS. 1-3 and described herein) with sampling chamber 46 being disposed therebetween. In optical system 60, optical elements 56 include a source mirror 62, a folding mirror 64, a turning mirror 66, a beam-splitter 68, detector mirrors 70 and 72, and/or other optical components.

Source mirror 62 is configured to direct electromagnetic radiation emitted by emitter 48 through first side 40 of the airway adapter through window 51 toward window 51 at second side 42 of the airway adapter. In some embodiments, source mirror 62 is a hyperbolic mirror.

Folding mirror 64 is configured to direct the emitted electromagnetic radiation back across sampling chamber 46 from second side 42 of the airway adapter toward first side 40 of the airway adapter such that the electromagnetic radiation passes back through window 51 on first side 40 of the airway adapter. In order to reduce the beam size of the electromagnetic radiation to a size that is manageable for detector 50, folding mirror 64 is a focusing mirror. The optical path from folding mirror 64 toward detector 50 is slightly transverse to the optical path from source mirror 62 to folding mirror 64. This is so that detector 50 is not positioned between source mirror 62 and folding mirror 64, which would tend to block some of the electromagnetic radiation emitted by emitter 48.

Turning mirror 66 is configured to direct electromagnetic radiation received back across sampling chamber 46 from folding mirror 64, and to direct the electromagnetic radiation onto beam-splitter 68. Turning mirror 66 may be a focusing mirror to further reduce the beam size of the electromagnetic radiation prior to the electromagnetic radiation becoming incident on beam-splitter 68.

Beam-splitter 68 is configured to divide the electromagnetic radiation into two separate beams that can be directed to sensors 52 and 54. Detector mirrors 70 and 72 are configured to receive the separate beams of electromagnetic radiation from beam-splitter 68, and to direct the separate beams of electromagnetic radiation onto sensors 52 and 54, respectively. Detector mirrors 70 and 72 may be focusing mirrors to reduce beam size prior to the electromagnetic radiation becoming incident on sensors 52 and 54. In some embodiments, beam splitter 68 is a dichroic beam splitter.

As was discussed above, the angle at which folding mirror 64 directs electromagnetic radiation back across sampling chamber 46 enables the reflected light to be received at first side 40 of the airway adapter without substantial overlap between incoming and outgoing electromagnetic radiation. This enables the incoming electromagnetic radiation to be received by turning mirror 66 without turning mirror 66 (or any other optical elements) from blocking the outgoing electromagnetic radiation. However, the responsive to folding mirror 64 being a spherical focusing mirror, the image of the emitted electromagnetic radiation produced by folding mirror 64 will be astigmatic. Such an image has two different focal points in two different planes. Said differently, the astigmatic image of a point source will have a line focus at one focal distance, a line focus at right angle to the first at a different focal distance, and out-of-focus blur in between. This comes about because the tilted folding mirror 64 has two apparent focal distances, one in a plane that includes the axis of tilt, the other in a plane at right angles to the first.

In order to correct for the astigmatic image caused by the tilting of folding mirror 64, optical elements 56 include at least one toric element. A toric element is an element having an optical surface that is a toroid section. The toric element may be, for example, folding mirror 64 or turning mirror 66. In some embodiments, detector mirror 70 and detector mirror 72 are each toric elements that correct for the astigmatic image in each of the beams of electromagnetic radiation created by beam-splitter 68 separately. It will be appreciated that the description of the at least one toric element being a reflective surface is not intended to be limiting. One or more toric lens elements may be included in the optical path of the electromagnetic radiation between emitter 48 and sensors 52 and 54. Other mechanisms for correcting the astigmatic image may be employed. Such mechanisms may include, for example, a block of IR transmissive material (e.g., glass or other materials) that is tilted, a holographic mirror, a counter tilted spherical mirror and/or other mechanisms. However, such mechanisms tend to be more bulky and/or costly than the proposed at least one toric element.

Figure 5:
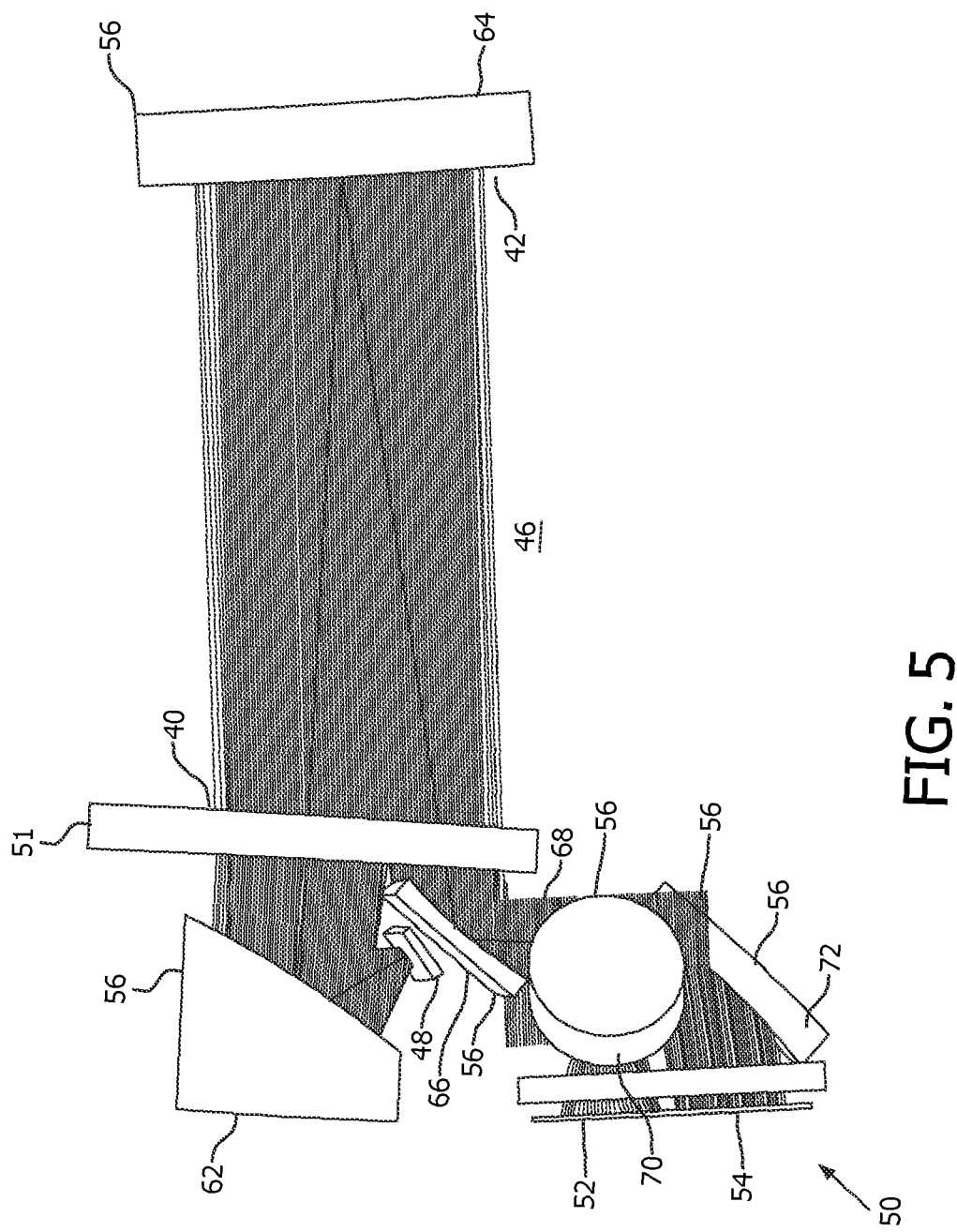
FIG. 5 illustrates an optical system of a gas measurement module.

FIG. 5 illustrates a different view of a configuration of optical system 60 of gas measurement module 16 that is similar to the one depicted in FIG. 4. In FIG. 5, folding mirror 64 is used in place of window 51 on second side 42 of sampling chamber 46. It will be appreciate that this configuration could further be extended such that folding mirror 64 is carried by the airway adapter (e.g., airway adapter 22 shown in FIGS. 1-3), rather than gas measurement module 16. The substitution of folding mirror 64 for either of windows 51 and/or 38 may enhance form factor, simplify manufacture, reduce cost, and/or provide other enhancements. As was the case with the configuration of optical system 60 in FIG. 4, in FIG. 5 one or more of optical elements 56 are toric elements to correct for the astigmatic image created by the tilt of folding mirror 64.

Figure 6:
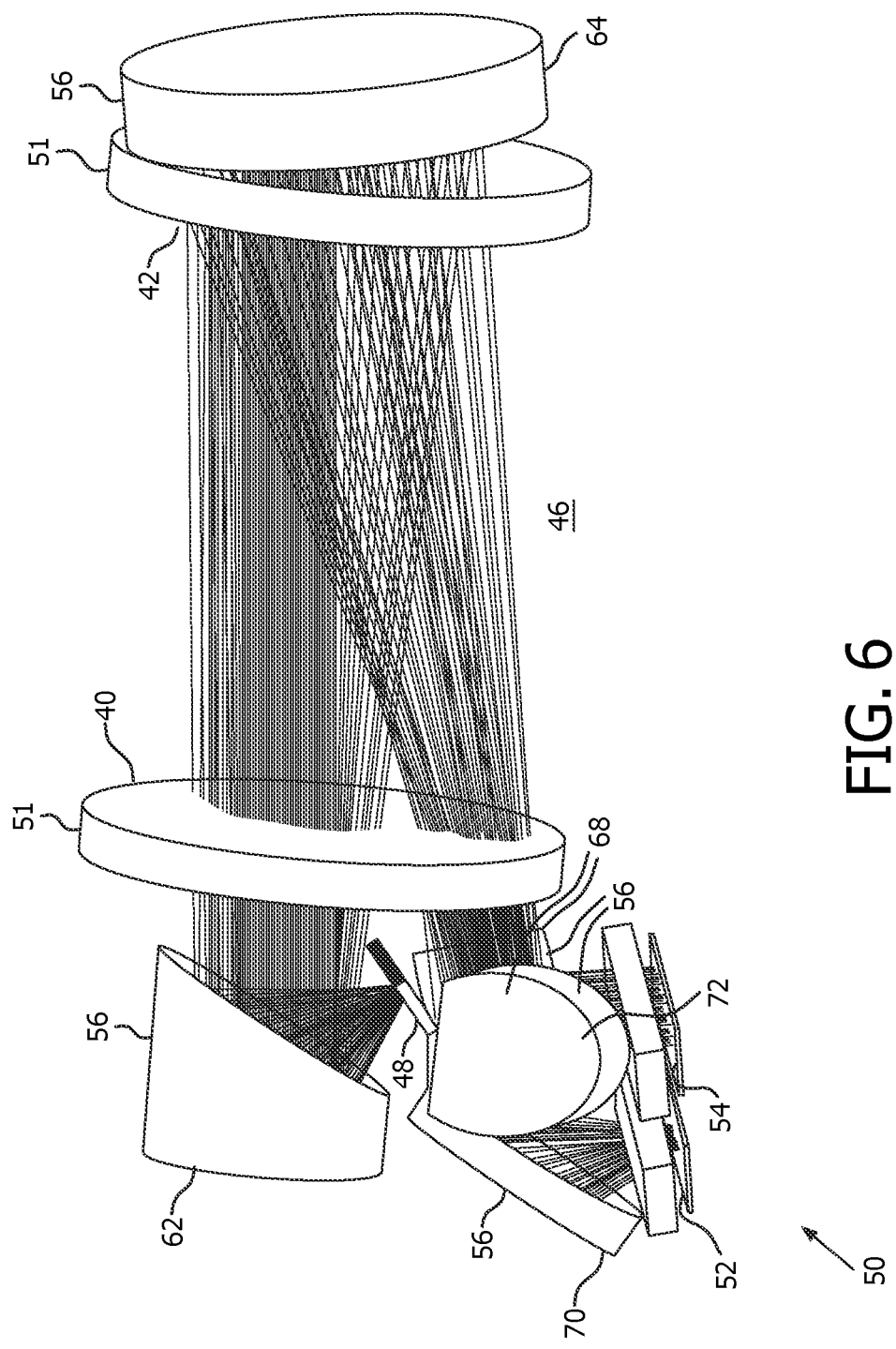
FIG. 6 illustrates an optical system of a gas measurement module.

FIG. 6 illustrates yet another configuration of optical system 60 of gas measurement module 16. In this configuration, optical elements 56 do not include turning mirror 66. Instead, electromagnetic radiation from folding mirror 64 that has gone back and forth across sampling chamber 46 is received onto beam-splitter 68 without being turned. In this configuration, the at least one toric element may include folding mirror 64 and/or detector mirror 70 and detector mirror 72.

Figure 7:
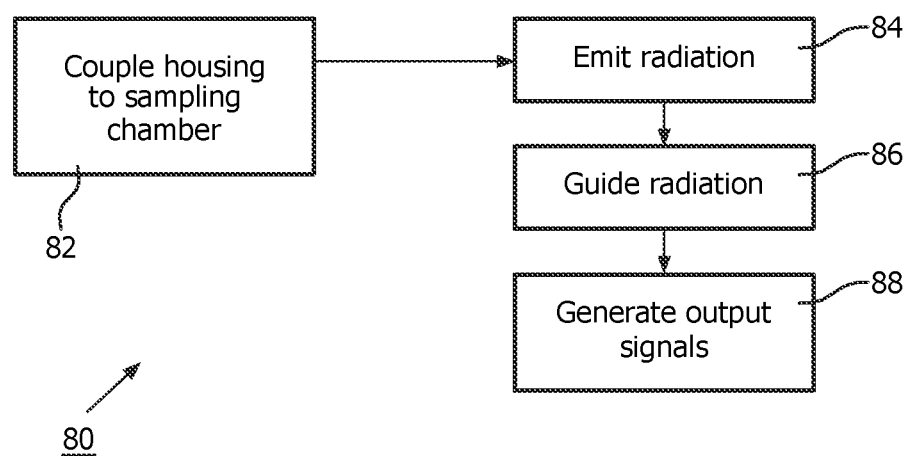
FIG. 7 illustrates a method of monitoring composition of a flow of breathable gas being delivered to a subject.

FIG. 7 illustrates a method 80 of monitoring composition of a flow of breathable gas within a respiratory circuit that is in fluid communication with an airway of a subject. The operations of method 80 presented below are intended to be illustrative. In some embodiments, method 80 may be accomplished with one or more additional operations not described, and/or without one or more of the operations discussed. Additionally, the order in which the operations of method 80 are illustrated in FIG. 7 and described below is not intended to be limiting.

At an operation 80, a housing is removably coupled to a sampling chamber. The sampling chamber has a first opening and a second opening, and is configured to form a flow path between the first opening and the second opening such that the flow of breathable gas within the respiratory circuit passes therethrough. The housing carries and/or houses an emitter, a detector, and optical elements. In some embodiments, the sampling chamber is the same as or similar to sampling chamber 46 (shown in FIGS. 1-6 and described herein) and the housing is the same as or similar to housing 44 (shown in FIGS. 1-3 and described herein).

At an operation 82, infrared radiation is emitted by the emitter. In some embodiments, the emitter is the same as or similar to emitter 48 (shown in FIGS. 1-6 and described herein).

At an operation 84, the emitted radiation is guided through a first side of the sampling chamber, across the sampling chamber to a second side of the sampling chamber that is opposite to the first side of the sampling chamber, back across the sampling chamber to the first side of the sampling chamber, and onto the detector. In some embodiments, operation 84 is performed by the optical elements, which may be the same as or similar to optical elements 56 (shown in FIGS. 3-6 and described herein).

At an operation 86, output signals are generated by the detector that convey information related to one or more parameters of the electromagnetic radiation guided thereto at operation 84. Because the electromagnetic radiation has passed back and forth through the flow of breathable gas within the sampling chamber, the output signals may convey information related to composition of the gas within the sampling chamber. In some embodiments, the detector is the same as or similar to detector 50 (shown in FIGS. 3-6 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A gas measurement module configured to monitor composition of a flow of breathable gas within a respiratory circuit that is in fluid communication with an airway of a subject, the gas measurement module being configured to assemble with an airway adapter in fluid communication with the airway, the gas measurement module comprising:

an emitter configured to emit infrared electromagnetic radiation;

a detector configured to generate output signals conveying information related to one or more parameters of electromagnetic radiation that becomes incident thereon; and a plurality of optical elements configured to guide the electromagnetic radiation emitted by the emitter through a sampling chamber of the airway adapter to the detector, wherein the sampling chamber has a first opening and a second opening, and is configured to form a flow path between the first opening and the second opening such that the flow of breathable gas within the respiratory circuit passes therethrough, and wherein the plurality of optical elements comprise a first optical element configured to guide the electromagnetic radiation emitted by the emitter through the sampling chamber via first and second airway adapter windows formed in substantially opposite sides of the airway adapter, a second optical element configured to reflect the electronic radiation from the second airway adapter window of the sampling chamber back through the sampling chamber via the second and first airway adapter windows, and a third optical element configured to reflect the electronic radiation emitted from the first airway adapter window of the sampling chamber to the detector such that the output signals generated by the detector convey information related to one or more parameters of the electromagnetic radiation that has traversed the sampling chamber and the flow of breathable gas therein twice, and wherein at least one of the optical elements is a toric element.

2. The gas measurement module of claim 1, wherein the second optical element comprises a folding mirror disposed adjacent the second airway adapter window of the sampling chamber, and wherein the folding mirror is the toric element.

3. The gas measurement module of claim 1, wherein the third optical element comprises a turning mirror for guiding the received electromagnetic radiation from the first airway adapter window toward the detector, and wherein the turning mirror is the toric element.

4. The gas measurement module of claim 1, wherein the detector comprises two separate photosensitive sensors, wherein the plurality of optical elements further comprise:

a beam splitter configured to receive the electromagnetic radiation that has traversed the sampling chamber and the flow of breathable gas therein twice; and two detector mirrors that receive electromagnetic radiation from the beam splitter and direct the electromagnetic radiation onto the two separate photosensitive sensors, and wherein the two detector mirrors are both toric elements.

5. The gas measurement module of claim 1, wherein the emitter, the detector, and the optical elements are carried within a housing that is removably coupled with the airway adapter forming the sampling chamber, the housing comprising first and second module mirrors that substantially align with the first and second airway adapter windows, respectively, when the housing is coupled with the airway adapter.

6. A method of monitoring composition of a flow of breathable gas within a respiratory circuit that is in fluid communication with an airway of a subject using a gas measurement module configured to assemble with an airway adapter of the respiratory circuit, the method comprising:

emitting infrared electromagnetic radiation from an emitter in the gas measurement module;

reflecting from a first optical element in the gas measurement module the electromagnetic radiation emitted by the emitter into a sampling chamber of the airway adapter through a first window of the sampling chamber, across the sampling chamber to a second window of the sampling chamber, wherein the first and second windows are on substantially opposite sides of the sampling chamber;

reflecting from a second optical element in the gas measurement module the electromagnetic radiation output from the second window back through the second window and across the sampling chamber to the first window of the sampling chamber; and reflecting from a third optical element in the gas measurement module the electromagnetic radiation output from the first window onto a detector measurement module, wherein the sampling chamber has a first opening and a second opening, and is configured to form a flow path between the first opening and the second opening such that the flow of breathable gas within the respiratory circuit passes therethrough such that the electromagnetic radiation passes back and forth across the flow path and the flow of breathable gas therein, and wherein the at least one of the reflecting of the electromagnetic radiation is performed in part by at least one toric optical element; and generating output signals conveying information related to one or more parameters of the electromagnetic radiation that has traversed the sampling chamber and the flow of breathable gas therein twice.

7. The method of claim 6, wherein the at least one toric optical element comprises a folding mirror disposed at or near the second window of the sampling chamber.

8. The method of claim 6, wherein the at least one toric optical element comprises a turning mirror disposed at or near the first window, and is configured to receive the electromagnetic radiation that has traversed the sampling chamber and the flow of breathable gas therein twice, and to guide the received electromagnetic radiation toward the detector.

9. The method of claim 8, further comprising:

splitting the electromagnetic radiation reflected by the turning mirror, wherein the detector comprises two separate photosensitive sensors; and wherein the at least one toric optical element comprises reflecting the split electromagnetic radiation using two detector mirrors to direct the split electromagnetic radiation onto the two separate photosensitive sensors, respectively.

10. The method of claim 6, further comprising:

removably coupling a housing to the sampling chamber, wherein the housing carries the emitter, the detector, and the at least one toric optical element.

11. A system for monitoring composition of a flow of breathable gas within a respiratory circuit that is in fluid communication with an airway of a subject, the system being connectable to the respiratory circuit, the system comprising:

means for emitting infrared electromagnetic radiation;

means for generating output signals conveying information related to one or more parameters of electromagnetic radiation that becomes incident thereon; and means for guiding the electromagnetic radiation emitted by the emitter into a sampling chamber of an airway adapter of the respiratory circuit through a first window of the airway adapter, across the sampling chamber and out a second window of the airway adapter that is on an opposite side of the airway adapter from the first window, for guiding the electromagnetic radiation from the second window back across the sampling chamber through the second window and out the first window of the sampling airway adaptor, and for reflecting the electromagnetic radiation from the first window onto the means for generating such that the output signals convey information related to one or more parameters of the electromagnetic radiation that has traversed the sampling chamber and the flow of breathable gas twice, wherein the sampling chamber has a first opening and a second opening, and is configured to form a flow path between the first opening and the second opening such that the flow of breathable gas within the respiratory circuit passes therethrough such that the electromagnetic radiation passes back and forth via the first and second windows across the flow path and the flow of breathable gas therein, and wherein the means for guiding includes at least one toric optical element.

12. The system if claim 11, wherein the at least one toric optical element comprises a folding mirror disposed at or near the second window of the airway adaptor for reflecting the electromagnetic radiation from the second window back across the sampling chamber.

13. The system of claim 11, wherein the at least one toric optical element comprises a turning mirror disposed at or near the first window of the airway adaptor, and configured to receive the electromagnetic radiation that has traversed the sampling chamber and the flow of breathable gas therein twice, and to reflect the received electromagnetic radiation toward the means for generating.

14. The system of claim 13, further comprising:

means for splitting the electromagnetic radiation reflected form the turning mirror, wherein the means for generating comprises two separate photosensitive sensors; and wherein the at least one toric optical element comprises two detector mirrors configured to separately receive the split electromagnetic radiation and to direct the split electromagnetic radiation onto the two separate photosensitive sensors, respectively.

15. The system of claim 11, further comprising:

means for housing the means for emitting, the means for generating, and the means for guiding; and means for removably coupling the means for housing to the sampling chamber.

* * * * *